United States Patent
Ho

(10) Patent No.: US 11,826,253 B2
(45) Date of Patent: *Nov. 28, 2023

(54) PERCUTANEOUS TEMPORARY AORTIC VALVE

(71) Applicant: HOCOR Cardiovascular Technologies LLC, Honolulu, HI (US)

(72) Inventor: Paul C. Ho, Honolulu, HI (US)

(73) Assignee: HOCOR CARDIOVASCULAR TECHNOLOGIES LLC, Honolulu, HI (US)

( * ) Notice: Subject to any disclaimer, the term of this patent is extended or adjusted under 35 U.S.C. 154(b) by 267 days.

This patent is subject to a terminal disclaimer.

(21) Appl. No.: 16/934,853

(22) Filed: Jul. 21, 2020

(65) Prior Publication Data

US 2021/0169641 A1   Jun. 10, 2021

Related U.S. Application Data

(63) Continuation of application No. 15/821,056, filed on Nov. 22, 2017, now Pat. No. 10,751,181, which is a
(Continued)

(51) Int. Cl.
*A61F 2/24* (2006.01)

(52) U.S. Cl.
CPC ............ *A61F 2/246* (2013.01); *A61F 2/2412* (2013.01); *A61F 2/2427* (2013.01);
(Continued)

(58) Field of Classification Search
CPC ...... A61F 2/2427; A61F 2/246; A61F 2/2466; A61F 2250/0059; A61F 2250/0067
See application file for complete search history.

(56) References Cited

U.S. PATENT DOCUMENTS

| | | |
|---|---|---|
| 3,671,979 A | 6/1972 | Moulopoulos et al. |
| 4,056,854 A | 11/1977 | Boretos et al. |

(Continued)

FOREIGN PATENT DOCUMENTS

| | | |
|---|---|---|
| WO | WO-9619159 A1 | 6/1996 |
| WO | WO-2014114798 A1 | 7/2014 |
| WO | WO-2016160765 A1 | 10/2016 |

OTHER PUBLICATIONS

Aksoy, et al. Myocardial ischemia in severe aortic regurgitation despite angiographically normal coronary arteries. Tohoku J Exp Med. 2012;226(1):69-73.

(Continued)

*Primary Examiner* — Brooke Labranche
(74) *Attorney, Agent, or Firm* — Wilson Sonsini Goodrich & Rosati

(57) ABSTRACT

Methods and apparatuses for regulating aortic regurgitation are provided. A catheter shaft is advanced through vasculature so that a flexible occluding membrane coupled to the catheter shaft is positioned within the aorta, typically the ascending aorta above the Sinus of Valsalva and coronary ostia. Blood flow in the aorta causes the flexible occluding membrane to alternate between an expanded occluding configuration while in diastole and a collapsed lesser occluding configuration is systole. The flexible occluding membrane thereby acts as a temporary aortic valve. The flexible occluding membrane is generally conical in shape, with the tip of the cone disposed closer to the aorta than the proximal rim. In diastole, blood flow expands the flexible occluding membrane so that the proximal rim apposes the inner wall of the aorta. The flexible occluding membrane will have one or more openings to allow perfusion of the coronary arteries in diastole.

12 Claims, 9 Drawing Sheets

Related U.S. Application Data continuation of application No. 15/083,768, filed on Mar. 29, 2016, now Pat. No. 9,855,143.

(60) Provisional application No. 62/140,111, filed on Mar. 30, 2015.

(52) U.S. Cl.
CPC .......... *A61F 2/2454* (2013.01); *A61F 2/2466* (2013.01); *A61F 2230/0008* (2013.01); *A61F 2230/0067* (2013.01); *A61F 2250/0059* (2013.01)

(56) References Cited

U.S. PATENT DOCUMENTS

| | | | |
|---|---|---|---|
| 6,989,027 | B2 | 1/2006 | Allen et al. |
| 8,211,165 | B1 | 7/2012 | McIntosh et al. |
| 8,663,318 | B2 | 3/2014 | Ho |
| 8,663,319 | B2 | 3/2014 | Ho |
| 9,308,086 | B2 | 4/2016 | Ho |
| 9,480,564 | B2 | 11/2016 | Ho |
| 9,700,410 | B2 | 7/2017 | Ho |
| 9,855,143 | B2 | 1/2018 | Ho |
| 10,751,181 | B2 | 8/2020 | Ho |
| 2004/0225354 | A1 | 11/2004 | Allen et al. |
| 2006/0074483 | A1 | 4/2006 | Schrayer |
| 2006/0178731 | A1 | 8/2006 | Tower |
| 2006/0265053 | A1 | 11/2006 | Hunt |
| 2007/0118209 | A1 | 5/2007 | Strecker et al. |
| 2009/0030503 | A1 | 1/2009 | Ho |
| 2009/0030510 | A1 | 1/2009 | Ho |
| 2010/0268017 | A1 | 10/2010 | Siess |
| 2012/0116439 | A1 | 5/2012 | Ho |
| 2012/0130468 | A1 | 5/2012 | Khosravi et al. |
| 2012/0179033 | A1 | 7/2012 | Merhi |
| 2014/0005540 | A1* | 1/2014 | Merhi .................. A61M 5/007 606/200 |
| 2014/0228940 | A1 | 8/2014 | McKinnis et al. |
| 2014/0277096 | A1* | 9/2014 | Richter .................. A61F 2/013 606/200 |

OTHER PUBLICATIONS

Ardehali, et al. Coronary blood flow reserve in acute aortic regurgitation. J Am Coll Cardiol. May 1995;25(6):1387-92.

Davies, et al. Evidence of a dominant backward-propagating "suction" wave responsible for diastolic coronary filling in humans, attenuated in left ventricular hypertrophy. Circulation. Apr. 11, 2006;113(14):1768-78. Epub Apr. 3, 2006.

"European Search Report dated Oct. 10, 2018 for EP167739665".

Ho, et al. Percutaneous Temporary Aortic Valve: A Proof-of-Concept Animal Model. J Heart Valve Dis 2013; 22:4; 460-467.

Ho, Paul C. Percutaneous aortic valve replacement (part 2): Miniaturization of the delivery system based on the novel temporary valve technology. Minim Invasive Ther Allied Technol. 2009; 18:3;172-177.

Ho, Paul C. Percutaneous aortic valve replacement (part 3): Balloon counterpulsation of a novel temporary aortic valve. Minim Invasive Ther Allied Technol. 2011; 20:101-106.

Ho, Paul C. Qualitative haemodynamic validation of a percutaneous temporary aortic valve: a proof of concept study. J Med Eng Technol. 2011; 35:2; 115-120.

Ho. Percutaneous aortic valve replacement: a novel design of the delivery and deployment system. Minim Invasive Ther Allied Technol. 2008;17(3):190-194.

International Search Report and Written Opinion dated Aug. 12, 2016 for International PCT Patent Application No. PCT/US2016/024637.

Moulopoulos, et al. Catheter-mounted aortic valves. Ann Thorac Surg. May 1971;11(5):423-30.

Moulopoulos, et al. Intra-aortic balloon pump for relief of aortic regurgitation. J Thorac Cardiovasc Surg. Jul. 1980;80(1):38-44.

Notice of Allowance dated Aug. 23, 2017 for U.S. Appl. No. 15/083,768.

Office Action dated Jul. 17, 2017 for U.S. Appl. No. 15/083,768.

Phillips, et al. A temporary catheter-tip aortic valve: hemodynamic effects on experimental acute aortic insufficiency. Ann Thorac Surg. Feb. 1976;21(2):134-7.

Quaden, et al. Percutaneous aortic valve replacement: resection before implantation. Eur J Cardiothorac Surg. May 2005;27(5):836-40.

Salizzoni, et al. Transapical off-pump removal of the native aortic valve: A proof-of-concept animal study. J Thorac Cardiovasc Surg, Aug. 2009;138:468-473.

U.S. Appl. No. 15/821,056 Notice of Allowance dated Apr. 22, 2020.

U.S. Appl. No. 15/821,056 Office Action dated Dec. 13, 2019.

U.S. Appl. No. 15/821,056 Office Action dated Mar. 23, 2020.

Wendt, et al. In vitro results of a new minimally invasive aortic valve resecting tool. Eur J Cardiothorac Surg. Apr. 2009;35(4):622-7; discussion 627. doi: 10.1016/j.ejcts.2009.01.005. Epub Feb. 23, 2009.

* cited by examiner

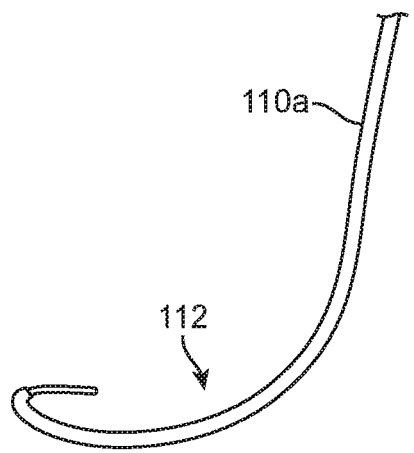
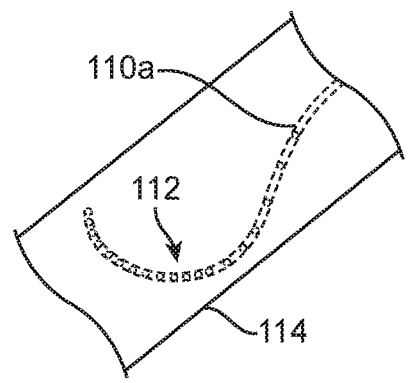
FIG. 1E                FIG. 1F
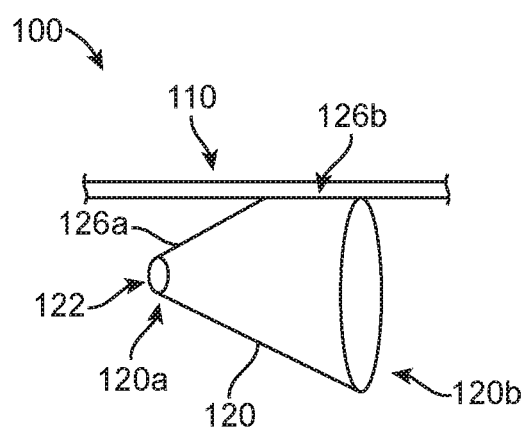
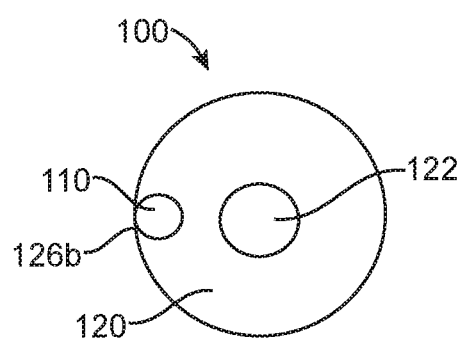
FIG. 1G                FIG. 1H Table 1. Fluid Volume Distribution over a 1-minute run

| | No AR | Severe AR | + 35% TAV gap | + 15% TAV gap | +0% TAV gap | P value |
|---|---|---|---|---|---|---|
| Forward Volume (l) | 21.12 +/- 0.49 | 14.43 +/- 0.18 | 15.23 +/- 0.32 | 15.81 +/- 0.20 | 17.46 +/- 0.09 | < 0.001 |
| Coronary Volume (l) | 1.97 +/- 0.06 | 1.78 +/- 0.01 | 1.78 +/- 0.01 | 1.78 +/- 0.01 | 1.76 +/- 0.02 | 0.912 |
| Regurgitant Volume (l) | 0 | 8.07 +/- 0.08 | 6.89 +/- 0.05 | 5.41 +/- 0.15 | 4.00 +/- 0.05 | < 0.001 |
| Coronary / Regurgitant Vol. | maximal | 0.22 +/- 0.00 | 0.26 +/- 0.01 | 0.33 +/- 0.01 | 0.44 +/- 0.01 | < 0.001 |
| Cycles (RPM) | 12 | 12 | 12 | 12 | 12 | | l = liters; RPM = revolutions per minute; AR = aortic regurgitation; TAV = temporary aortic valve; p < 0.05 = statistical significance

FIG. 6

PERCUTANEOUS TEMPORARY AORTIC VALVE

CROSS-REFERENCE

This application is a continuation of U.S. patent application Ser. No. 15/821,056, filed Nov. 22, 2017, now U.S. Pat. No. 10,751,181; which is a continuation of U.S. patent application Ser. No. 15/083,768, filed Mar. 29, 2016, now U.S. Pat. No. 9,855,143; which claims the benefit of U.S. Provisional Patent Application No. 62/140,111, filed Mar. 30, 2015; the full contents of which are incorporated herein by reference.

The subject matter of this application is related to the subject matter of the following co-assigned patents and pending patent applications: U.S. patent application Ser. No. 11/781,924 (filed on Jul. 23, 2007 and issued on Mar. 4, 2014 as U.S. Pat. No. 8,663,318), Ser. No. 12/180,223 (filed on Jul. 25, 2008 and issued on Mar. 4, 2014 as U.S. Pat. No. 8,663,319), Ser. No. 13/227,276 (filed on Sep. 7, 2011), Ser. No. 14/154,890 (filed on Jan. 14, 2014), and Ser. No. 14/155,060 (filed on Jan. 14, 2014), the full contents of which are incorporated herein by reference.

BACKGROUND

The present disclosure relates to medical devices, systems, and methods. In particular, the present disclosure relates to the percutaneous delivery and deployment of a temporary aortic valve to facilitate other percutaneous procedures such as the delivery of aortic replacement valves or to serve as a standalone hemodynamic support device when the native aortic valve is damaged from infective endocarditis or trauma, for example. The native aortic valve damage may also be iatrogenic from deliberate valve resection prior to valve placement.

The native aortic valve can fail acutely from infection or mechanical trauma. In endocarditis of the aortic valve, the timing for surgery may be limited during the active phase of the infection. The condition can be fatal as significant acute aortic regurgitation may cause decompensating heart failure. Mechanical failure of the aortic valve can occur from proximal aortic dissection or direct leaflet and/or annular tear with similar potential lethal outcome. Patients suffering from significant aortic valve disease are frequently treated by aortic valve replacement procedures. While most aortic valve replacements are still performed in open chest procedures, recently there have been significant advances in minimally invasive aortic valve replacement where the valve is introduced through a transapical approach (minimally invasive), a transaortic approach (minimally invasive), or a transvascular (percutaneous) approach over the aortic arch. In the era of transcatheter aortic valve intervention (TAVI), iatrogenic damage to the aortic valve may become relevant especially with suggestions for valve resection prior to replacement. The clinical needs for a percutaneous temporary aortic valve are therefore apparent.

Transapical, transaortic, and transfemoral percutaneous aortic valve procedures are "beating heart" procedures where continuing blood flow from the left ventricle into the aorta creates hemodynamic forces on the replacement valves and the tools used in the replacement procedures. In an effort to control the hemodynamic forces and to stabilize the tools and valve used for replacement, that the use of a "temporary aortic valve" (TAV) has recently been proposed. As described in commonly owned published U.S. Patent Publications Nos. US 2009/0030503, US 2009/0030510 and US 2012/0116439, the full disclosures of which are incorporated herein by reference, a catheter is intravascularly introduced over the aortic arch to position a balloon assembly in the ascending aorta just above the Sinus of Valsalva. The balloon assembly includes three equally sized balloons disposed in parallel about the distal tip of the catheter, and the inflated balloons together limit retrograde blood flow (flow in the direction from the aorta toward the aortic valve) during diastole, thus limiting disturbance of the tools and/or valves located in the aortic valve annulus during the procedure. The balloon inflation only partially occludes the aortic lumen in order to both allow antegrade flow during systole and to permit a limited retrograde flow during diastole in order to perfuse the coronary vasculature through the Sinus of Valsalva and to protect the left ventricle from excessive volume overload. As a standalone procedure, in cases of naturally occurring damage (as opposed to iatrogenic) of the native aortic valve such as from infective endocarditis or trauma, the temporary aortic valve can also be placed similarly in the ascending aorta as a hemodynamic support device.

While of great potential benefit, the use of the fixed-balloon structures described in the prior patent applications is necessarily a compromise between resistance to regurgitation during diastole and forward blood flow patency through the aorta during systole. Even when the balloons are collapsed to their minimum cross-sectional area in a counter-pulsating balloon system, the complex balloon structures may be cumbersome to advance through tortuous vasculature and may be prone to mechanical failure, particularly due to the relatively high number of mechanical elements and after repeated cycles of expansion and collapse.

Previous models of catheter-based temporary aortic valves for the treatment of acute aortic regurgitation have also not reached clinical relevance mostly due to their inability to adequately protect coronary circulation. When deployed in the ascending aorta, the compromised diastolic coronary flow from acute aortic regurgitation has been shown to further reduce from the occlusive nature of the device designs. Myocardial ischemia can occur in acute aortic regurgitation alone without concomitant coronary artery disease. Coronary flow obstruction by the temporary aortic valve should therefore be overcome in improved device designs.

For these reasons, it would be desirable to provide improved methods and systems for occluding the aorta to limit aortic regurgitation during valve repair and replacement procedures as well as to provide a standalone device for hemodynamic support in the native aortic valve when damaged by naturally occurring aortic regurgitation, such as from infective endocarditis or trauma. In at least the latter application, the methods and systems can be a life-saving bridge to open heart surgery to correct the aortic valve damage.

The following references may be of interest:

Aksoy S, Cam N, Guney MR, Gurkan U, Oz D, Poyraz E, Eksik A, Agirbasli M. Myocardial ischemia in severe aortic regurgitation despite angiographically normal coronary arteries. *Tohoku J Exp Med* 2012;226(1):69-73.

Ardehali A, Segal J, Cheitlin M. Coronary blood flow reserve in acute aortic regurgitation. *J Am Coll Cardiol* 1995;25:1387-1392.

Davies J E, Whinnett Z I, Francis D P, Manisty C H, Aguardo-Sierra J, Willson K, Foale R A, Malik I S, Hughes A D, Parker K H, Mayet J. Evidence of a dominant backward-propagating "suction" wave responsible for diastolic coronary filling in humans, attenuated in left ventricular hypertrophy. *Circulation* 2006; 113 (14): 1768-78.

Ho PC. Percutaneous aortic valve replacement: a novel design of the delivery and deployment system. *Minim Invasive Ther Allied Technol* 2008;17(3):190-194.

Ho PC. Percutaneous aortic valve replacement (part 2): An innovative approach to miniaturize the delivery system based on the novel temporary valve technology. *Minim Invasive Ther Allied Technol* 2009; 18(3): 172-177.

Ho PC. Percutaneous aortic valve replacement (part 3): Counterpulsation temporary valve technology. *Minim Invasive Ther Allied Technol* 2011;20(2):101-106.

Ho PC. Qualitative hemodynamic validation of a percutaneous temporary aortic valve; a proof of concept study. *J Med Eng Technol* 2011;35(2):115-120.

Ho P C, Nguyen M E, Golden P J. Percutaneous temporary aortic valve: a proof-of-concept animal model. *J Heart Valve Dis* 2013;22:460-467.

Moulopoulos S D, Anthopoulos L, Stamatelopoulos S, Stefadouros M, Catheter-mounted aortic valves. *Ann Thorac Surg* 1971;11(5):423-430.

Moulopoulos S D, Anthopoulos L, Antonatos P G, Adamopoulos P N, Nanas J N. Intraaortic balloon pump for relief of aortic regurgitation. *J Thorac Cardiovasc Surg* 1980;80:38-44.

Phillips S J, Ciborski M, Freed P S, Cascade P N, Jaron D. A temporary catheter-tip aortic valve: hemodynamic effects on experimental acute aortic insufficiency. *Ann Thorac Surg* 1976 Feb;21(2):134-7.

Quaden R, Attmann T, Boening A, Cremer J, Lutter G. Percutaneous aortic valve replacement: Resection before impintation. *Eur J Cardiothorac Surg* 2005;27:836-840.

Salizzoni S, Bajona P, Zehr K J, Anderson W D, Vandenberghe S, Speziali G. Transapical off-pump removal of the native aortic valve; a proof-of-concept animal study. *J Thorac Cardiovasc Surg* 2009;138(2):468-473.

Wendt D, Müller W, Hauck F, Thielmann M, Wendt H, Kipfmüller B, Vogel B, Jakob H. In vitro results of a new minimally invasive aortic valve resecting tool. *Eur J Cardiothorac Surg* 2009;35(4):622-627.

SUMMARY

The issues discussed above and others may be addressed by the devices, systems, and methods of the present disclosure.

A novel percutaneous transcatheter temporary aortic valve (TAV) is presented. The valve may include a cone-shaped membrane based occlusion element. In ventricular systole, the occlusion element may collapse to reduce aortic obstruction. In ventricular diastole, the occlusion element may expand to occlude the aorta to inhibit regurgitation while allowing coronary filling through a gap or opening in the occlusion element. The diastolic gap or opening may have a variety of sizes to balance adequate coronary flow with protection against acute regurgitation. In contrast with prior occlusive devices, there is typically no fixed gap size for the membrane based occlusion element in systole. By removing the systolic obstructive component of a fixed gap, the membrane based occlusion element's diastolic gap size can be smaller to provide better protection against acute regurgitation. A lower limit of the gap:aorta cross-sectional area ratio can be redefined based on adequate coronary flow. For example, based on experimental results and/or mathematical models, the size of the diastolic gap or opening may be selected to optimize coronary filing while protecting against aortic regurgitation.

Aspects of the present disclosure provide temporary aortic valve apparatuses which may comprise a catheter shaft and a flexible occluding membrane. The catheter shaft may be adapted to be advanced through a vasculature of a patient for placement within an aorta or other blood vessel of the patient. The flexible occluding membrane may have a lateral side coupled to the catheter shaft and may be adapted to alternate between an expanded occluding configuration and a collapsed lesser occluding configuration in the aorta or other blood vessel in synchrony with ventricular diastole and systole.

The flexible occluding membrane may be adapted to assume the expanded occluding configuration in response to blood flow in the aorta during ventricular diastole. The flexible occluding membrane may be adapted to assume the collapsed lesser occluding configuration in the aorta in response to blood flow therein during ventricular systole.

The flexible occluding membrane may have an opening to allow blood perfusion therethrough when in the expanded occluding configuration. The opening may be positioned at substantially a center of the flexible occluding membrane. The opening and the center of the flexible occluding membrane may be disposed at a distal tip of the flexible occluding membrane. Alternatively or in combination, the opening may be positioned at a location offset from a center of the flexible occluding membrane. The flexible occluding membrane may have a plurality of openings to allow blood perfusion therethrough when in the expanded occluding configuration. The opening(s) may have a variety of cross sectional sizes. For example, the opening(s) may have a cross-sectional size of 50% or less, 45% or less, 40% or less, 35% or less, 30% or less, 25% or less, 20% or less, 15% or less, 10% or less, or 5% or less, to name of few sizes, of the aorta or other blood vessel.

The catheter shaft may further comprise a distal anchoring loop. The distal anchoring loop may have an expanded, curved configuration and a collapsed, straightened configuration. In the expanded, curved configuration, the distal anchoring loop may anchor the catheter shaft and the flexible occluding membrane in the aorta or other blood vessel. For example, the distal anchoring loop may be sized to appose and/or exert a radially outward force on the inner wall of the aorta or other blood vessel when in the expanded, curved configuration, thereby anchoring the catheter shaft and the flexible occluding membrane in place. In the collapsed, straightened configuration, the distal anchoring loop may be in a smaller cross-section configuration to facilitate the advancement and removal of the catheter shaft and the flexible occluding membrane.

The flexible occluding membrane may have a conical shape. The conically-shaped flexible occluding membrane may comprise an annular proximal lip adapted to appose an inner wall of the aorta when the flexible occluding membrane is in the expanded occluding configuration. The conical shape of the flexible occluding membrane may be oriented with the larger opening (proximal lip) away from the aortic valve. The flexible occluding membrane may be adapted to be positioned within an ascending aorta of the patient to provide occlusion therein. The flexible occluding membrane may be adapted to be positioned within the ascending aorta just above the Sinus of Valsalva and coronary ostia. For example, the diameter of the annular proximal lip may be selected to closely match or exceed that of a typical human ascending aorta above the Sinus of Valsalva and coronary ostia.

Aspects of the present disclosure also provide temporary aortic valve apparatuses comprising a catheter shaft and a flexible occluding membrane having an opening to allow blood perfusion therethrough when the membrane is in an expanded configuration. The catheter shaft may be adapted to be advanced through a vasculature of a patient for placement within an aorta or other blood vessel of the patient. The flexible occluding membrane may be coupled to the catheter shaft and adapted to alternate between an expanded occluding configuration and a collapsed lesser occluding configuration in the aorta in synchrony with ventricular diastole and systole.

The catheter shaft and the flexible occluding membrane may be coupled to one another at a center of the flexible occluding membrane or at a location offset from a center of the flexible occluding membrane.

The flexible occluding membrane may be adapted to assume the expanded occluding configuration in response to blood flow in the aorta during ventricular diastole. The flexible occluding membrane may be adapted to assume the collapsed lesser occluding configuration in the aorta in response to blood flow therein during ventricular systole.

The opening may be positioned at substantially a center of the flexible occluding membrane. The opening and the center of the flexible occluding membrane may be disposed at a distal tip of the flexible occluding membrane. The opening may be positioned at a location offset from a center of the flexible occluding membrane. The flexible occluding membrane may have a plurality of openings to allow blood perfusion therethrough when in the expanded occluding configuration. The opening(s) may have a variety of cross sectional sizes. For example, the opening(s) may have a cross-sectional size of 50% or less, 45% or less, 40% or less, 35% or less, 30% or less, 25% or less, 20% or less, 15% or less, 10% or less, or 5% or less, to name of few sizes, of the aorta or other blood vessel.

The catheter shaft may comprise a distal anchoring loop. The distal anchoring loop may have an expanded, curved configuration and a collapsed, straightened configuration. In the expanded, curved configuration, the distal anchoring loop may anchor the catheter shaft and the flexible occluding membrane in the aorta or other blood vessel. For example, the distal anchoring loop may be sized to appose and/or exert a radially outward force on the inner wall of the aorta or other blood vessel when in the expanded, curved configuration, thereby anchoring the catheter shaft and the flexible occluding membrane in place. In the collapsed, straightened configuration, the distal anchoring loop may be in a smaller cross-section configuration to facilitate the advancement of the catheter shaft and the flexible occluding membrane.

The flexible occluding membrane may have a conical shape. The conically-shaped flexible occluding membrane may comprise an annular proximal lip adapted to appose an inner wall of the aorta when the flexible occluding membrane is in the expanded occluding configuration. The flexible occluding membrane may be adapted to be positioned within an ascending aorta of the patient to provide occlusion therein. The flexible occluding membrane may be adapted to be positioned within the ascending aorta just above the Sinus of Valsalva and coronary ostia. For example, the diameter of the annular proximal lip may be selected to closely match or exceed that of a typical human ascending aorta just above the Sinus of Valsalva and coronary ostia.

Aspects of the present disclosure may also provide methods for regulating aortic regurgitation during an aortic valve diagnostic or treatment procedure. A catheter shaft may be advanced through a vasculature of a patient so that a flexible occluding membrane having a lateral side coupled to the catheter shaft is positioned within an aorta or other blood vessel of the patient. Blood flow in the aorta may cause the flexible occluding membrane to alternate between an expanded occluding configuration and a collapsed lesser occluding configuration in synchrony with ventricular diastole and systole. Blood flow in the aorta during ventricular diastole may cause the flexible occluding membrane to assume the expanded occluding position. The flexible occluding membrane may passively alternate between the configurations due to the blood flow, thereby obviating the need for any active, mechanical actuation of device and reducing risks of mechanical failure of the device. Expansion of the flexible occluding member during ventricular diastole may inhibit aortic regurgitation.

In advancing the catheter shaft, the flexible occluding membrane may be positioned within the ascending aorta above the Sinus of Valsalva and coronary ostia. Expansion of the flexible occluding member during ventricular diastole may inhibit aortic regurgitation while allowing perfusion of the coronary arteries via the Sinus of Valsalva. Perfusion of the coronary arteries via the Sinus of Valsalva may be allowed by an opening on the flexible occluding membrane. The opening may be positioned at a variety of locations. There may be more than one opening. The opening may be positioned at substantially a center of the flexible occluding membrane. The opening and the center of the flexible occluding membrane may be disposed at a distal tip of the flexible occluding membrane. The opening may be positioned at a location offset from a center of the flexible occluding membrane. Perfusion of the coronary arteries via the Sinus of Valsalva may be allowed by a plurality of openings on the flexible occluding membrane. The opening(s) may have a variety of cross sectional sizes. For example, the opening(s) may have a cross-sectional size of 50% or less, 45% or less, 40% or less, 35% or less, 30% or less, 25% or less, 20% or less, 15% or less, 10% or less, or 5% or less, to name of few, of the aorta or other blood vessel.

A distal anchoring loop of the catheter shaft may be expanded to a curved configuration to anchor the catheter shaft and the flexible occluding membrane in the aorta or other blood vessel. For example, the distal anchoring loop may be expanded to a size in which it apposes and/or exerts a radially outward force on the inner wall of the aorta or other blood vessel, thereby anchoring the catheter shaft and the flexible occluding membrane in place. The distal anchoring loop may have an expanded, curved configuration and a collapsed, straightened configuration. To advance or retract the distal anchoring loop, it may be collapsed and/or straightened to a lower cross-sectional area configuration.

The flexible occluding membrane may have a conical shape and an annular proximal lip. Blood flow in the aorta during diastole may cause the annular proximal lip to appose an inner wall of the aorta. Blood flow in the aorta during ventricular systole may cause the flexible occluding membrane to assume the collapsed lesser occluding configuration. Collapse of the flexible occluding membrane during ventricular systole may lessen inhibition of blood flow from a left ventricle of the patient to the aorta.

An aortic valve replacement or repair procedure may be performed while blood flow in the aorta continues to cause the flexible occluding membrane to alternate between the expanded occluding configuration and the collapsed lesser occluding configuration in synchrony with diastole and systole. An example of such a procedure may include the advancement of a replacement valve through a lumen of the catheter shaft.

The catheter shaft may be advanced over an aortic arch of the patient. The catheter shaft may be advanced or introduced to the aorta or other blood vessel transapically, transaortically, or transfemorally, to name a few approaches.

Aspects of the present disclosure may also provide methods for regulating aortic regurgitation during an aortic valve diagnostic or treatment procedure. A catheter shaft may be advanced through a vasculature of a patient so that a flexible occluding membrane coupled to the catheter shaft is positioned within an aorta or other blood vessel of the patient. Blood flow in the aorta may cause the flexible occluding membrane to alternate between an expanded occluding configuration and a collapsed lesser occluding configuration in synchrony with ventricular diastole and systole. Perfusion of the coronary arteries via the Sinus of Valsalva may be allowed by an opening on the flexible occluding membrane. Blood flow in the aorta or other blood vessel during ventricular diastole may cause the flexible occluding membrane to assume the expanded occluding position. The flexible occluding membrane may passively alternate between the configurations due to the blood flow, thereby obviating the need for any active, mechanical actuation of device and reducing risks of mechanical failure of the device. Expansion of the flexible occluding member during ventricular diastole may inhibit aortic regurgitation.

The opening may be positioned at a variety of locations. There may be more than one opening. The opening may be positioned at substantially a center of the flexible occluding membrane. The opening and the center of the flexible occluding membrane may be disposed at a distal tip of the flexible occluding membrane. The opening may be positioned at a location offset from a center of the flexible occluding membrane. Perfusion of the coronary arteries via the Sinus of Valsalva may be allowed by a plurality of openings on the flexible occluding membrane. The opening(s) may have a variety of cross sectional sizes. For example, the opening(s) may have a cross-sectional size of 50% or less, 45% or less, 40% or less, 35% or less, 30% or less, 25% or less, 20% or less, 15% or less, 10% or less, or 5% or less, to name of few, of the aorta or other blood vessel.

A distal anchoring loop of the catheter shaft may be expanded to a curved configuration to anchor the catheter shaft and the flexible occluding membrane in the aorta or other blood vessel. For example, the distal anchoring loop may be expanded to a size in which it apposes and/or exerts a radially outward force on the inner wall of the aorta or other blood vessel, thereby anchoring the catheter shaft and the flexible occluding membrane in place. The distal anchoring loop may have an expanded, curved configuration and a collapsed, straightened configuration. To advance or retract the distal anchoring loop, it may be collapsed and/or straightened to a lower cross-sectional area configuration.

In advancing the catheter shaft, the flexible occluding membrane may be positioned within the ascending aorta above the Sinus of Valsalva and coronary ostia. Expansion of the flexible occluding member during ventricular diastole may inhibit aortic regurgitation while allowing perfusion of the coronary arteries via the Sinus of Valsalva.

The flexible occluding membrane may have a conical shape and an annular proximal lip. Blood flow in the aorta during diastole may cause the annular proximal lip to appose an inner wall of the aorta. Blood flow in the aorta during ventricular systole may cause the flexible occluding membrane to assume the collapsed lesser occluding configuration. Collapse of the flexible occluding membrane during ventricular systole may lessen inhibition of blood flow from a left ventricle of the patient to the aorta.

An aortic valve replacement or repair procedure may be performed while blood flow in the aorta continues to cause the flexible occluding membrane to alternate between the expanded occluding configuration and the collapsed lesser occluding configuration in synchrony with diastole and systole. An example of such a procedure may include the advancement of a replacement valve through a lumen of the catheter shaft.

The catheter shaft may be advanced over an aortic arch of the patient. The catheter shaft may be advanced or introduced to the aorta or other blood vessel transapically, transaortically, or transfemorally, to name a few approaches.

The flexible occluding membrane may be coupled to the catheter shaft at a center of the flexible occluding membrane. The flexible occluding membrane may be coupled to the catheter shaft at a location of the flexible occluding membrane offset from a center of the flexible occluding membrane.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. It should be noted that the drawings are not to scale and are intended only as an aid in conjunction with the explanations in the following detailed description. In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings. A better understanding of the features and advantages of the present disclosure will be obtained by reference to the following detailed description that sets forth illustrative embodiments, in which the principles of the present disclosure are utilized, and the accompanying drawings of which:

FIG. 1E shows a perspective view of a distal end and the anchoring loop of the catheter shaft of the temporary aortic valve apparatus of FIG. 1A;

FIG. 1F shows a magnified view of the distal end and the anchoring loop of the catheter shaft of the valve apparatus of FIG. 1A placed in vessel;

FIG. 1G shows a side view of another temporary aortic valve apparatus, according to some embodiments;

FIG. 1H shows a front view of the temporary aortic valve apparatus of FIG. 1G;

FIG. 6 shows a table of fluid volume distributions of temporary aortic valve apparatuses tested in the testing apparatus of FIG. 4.

DETAILED DESCRIPTION

Figure 1A:
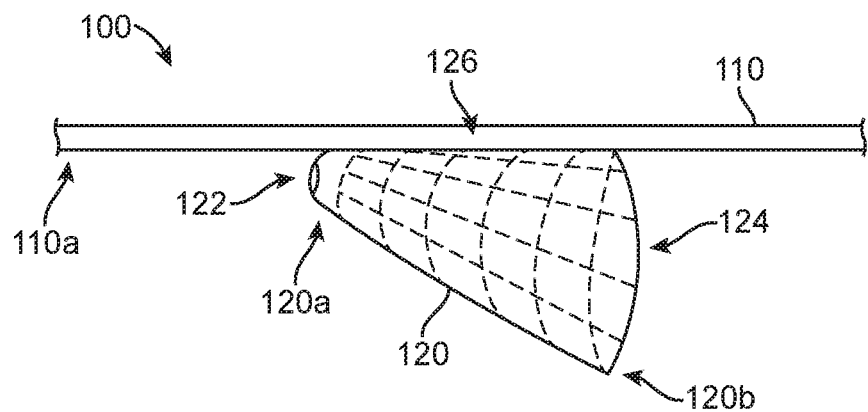
FIG. 1A shows a side view of a temporary aortic valve apparatus, according to some embodiments.
Figure 1B:
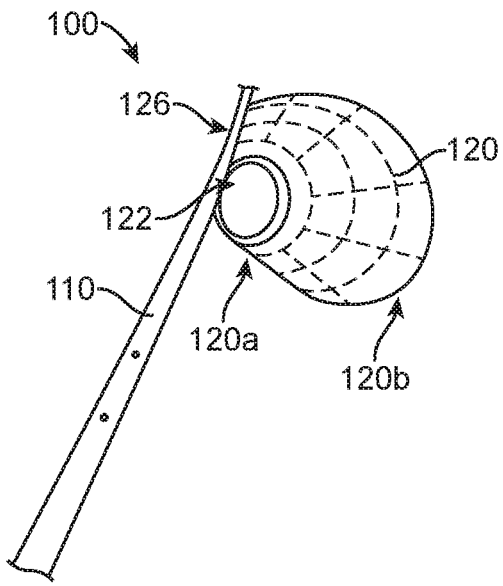
FIG. 1B shows a perspective view of the front of the temporary aortic valve apparatus of FIG. 1A.
Figure 1C:
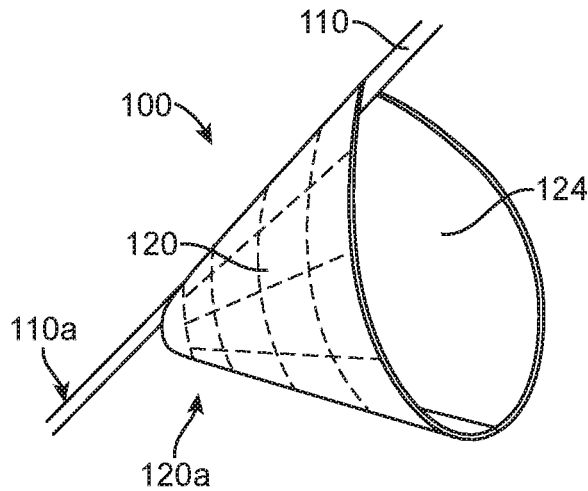
FIG. 1C shows a perspective view of the back and proximal lip of the temporary aortic valve apparatus of FIG. 1A.
Figure 1D:
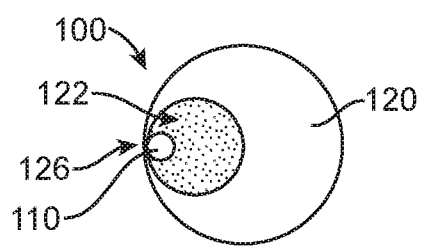
FIG. 1D shows a front view of the temporary aortic valve apparatus of FIG. 1A.

FIG. 1A shows a side view of a temporary aortic valve apparatus 100. FIG. 1B shows a perspective view of the front of the temporary aortic valve apparatus 100. FIG. 1C shows a perspective view of the back of the temporary aortic valve apparatus 100. FIG. 1D shows a front view of the temporary aortic valve apparatus 100. FIG. 1E shows a distal portion 110a of the temporary aortic valve apparatus 100. FIG. 1F shows the distal portion 110a of the temporary aortic valve apparatus 100 placed in a vessel. FIG. 1G shows a side view of an embodiment of the temporary aortic valve apparatus 100. FIG. 1H shows a front view of an embodiment of the temporary aortic valve apparatus 100.

The temporary aortic valve apparatus 100 may comprise a catheter shaft 110 and a flexible occluding membrane 120 attached to the catheter shaft 110. The flexible occluding membrane 120 may be attached to the catheter shaft 110 near the distal portion 110a of the catheter shaft 110. The flexible occluding membrane 120 may have an axially distal end 120a and an axially proximal end 120b. A lateral side 126 of the flexible occluding membrane 120 is attached to the catheter shaft 110 such that the flexible occluding membrane 120 is axially aligned with the catheter shaft 110, with both the distal end 120a and the proximal end 120b being attached to the flexible occluding membrane. As shown in FIGS. 1E and 1F, the distal portion 110a of the catheter shaft 110 may include a large distal loop 112 at the distal end to aid in anchoring the temporary aortic valve apparatus 100. The large distal loop 112 may include one or more radiopaque markers 114 to allow it to be visualized during a surgical procedure. FIG. 1F shows the large distal loop 112 anchoring the temporary aortic valve apparatus 100 in a vessel such as a blood vessel. The large distal loop 112 can appose the inner wall of the vessel and the friction therebetween can anchor the large distal loop 112 and the TAV 100 in place. In some embodiments, the large distal loop 112 is actuated between expanded and collapsed configurations so that that catheter shaft 110 can be engaged and disengaged from the vessel wall. In the collapsed configuration, the large distal loop 112 may be straightened by an advancable, internal guidewire or other mechanism. The collapsed (e.g., straightened) configuration of the loop 112 may facilitate the delivery of the TAV to the ascending aorta and/or its removal from the vasculature. The distal end portion 110a of the catheter shaft 110 may be pre-formed to have the large distal loop 112. When the straightening guide wire is removed, the large distal loop 112 may resiliently return to its curved shape. Alternatively, the large distal loop 112 can be pre-formed to be straight and can be curved or looped with the advancement of a guidewire with a curved end therethrough.

The flexible occluding membrane 120 may be expandable and collapsible. Generally, when placed in a bodily vessel such as a blood vessel, the direction of fluid flow may dictate whether the flexible occluding membrane 120 is in its expanded or collapsed configuration. The flexible occluding membrane 120 may be conical in shape, with the conical shape tapering toward the distal end 120a. The flexible occluding membrane 120 may have a large proximal opening or gap 124 such that fluid (e.g., blood) flow in the direction of the taper causes fluid to flow into the proximal opening 124 to cause the flexible occluding membrane 120 to expand. When expanded, the circumferential or annular lip on the proximal end 120b of the flexible occluding membrane 120 may appose the inner wall of the bodily vessel. Generally, the circumferential or annular lip on the proximal end 120b is sized such that when expanded, it fully apposes the annular inner wall of the bodily vessel such as the ascending aorta (i.e., the diameter of the distal end 120b when expanded may be greater or equal to the diameter of the inner wall of the target bodily vessel). The distal end 120a of the flexible occluding membrane 120 may have a smaller opening or gap 122 which allows some fluid to pass through the expanded flexible occluding membrane 120. The opening or gap 122 may be a cut-out section of the tip of the conical membrane 120. In some cases, the flexible occluding membrane 120 may be biased to be in the expanded configuration even without fluid flow in the direction of the taper. When fluid (e.g., blood) flows in the opposite direction, fluid flowing past the outer surface of the flexible occluding membrane 120 may urge the flexible occluding membrane 120 to collapse.

As shown in FIGS. 1A to 1D, the temporary aortic valve apparatus 100 may have the distal opening or gap 122 positioned closely relative to the catheter shaft 110. Other locations of the distal opening or gap 122 are also contemplated. As shown in FIGS. 1G and 1H, the opening or gap 122 may be spaced apart from the catheter shaft 110 while still being positioned at the distal tip 120a of the flexible occluding membrane 120. A proximal, lateral portion 126b of the flexible occluding membrane 120 is attached to the catheter shaft 110 while a distal lateral portion 126a of the flexible occluding membrane remains free. Further locations of the distal opening or gap 122 are also contemplated. For example, the distal opening or gap 122 may be slightly offset from the distal tip 120a of the flexible occluding membrane 120. While one distal opening or gap 122 is shown, having a plurality of distal openings or gaps is also contemplated. For example, there may be a plurality of distal openings or gaps 122 distributed about the distal tip 120a of the flexible occluding membrane in some embodiments.

As shown in FIGS. 1E and 1F, the distal portion 110a of the catheter shaft 110 may include a large distal loop 112 at the distal end to aid in anchoring the temporary aortic valve apparatus 100. The large distal loop 112 may include one or more radiopaque markers 114 to allow it to be visualized during a surgical procedure.

Figure 2A:
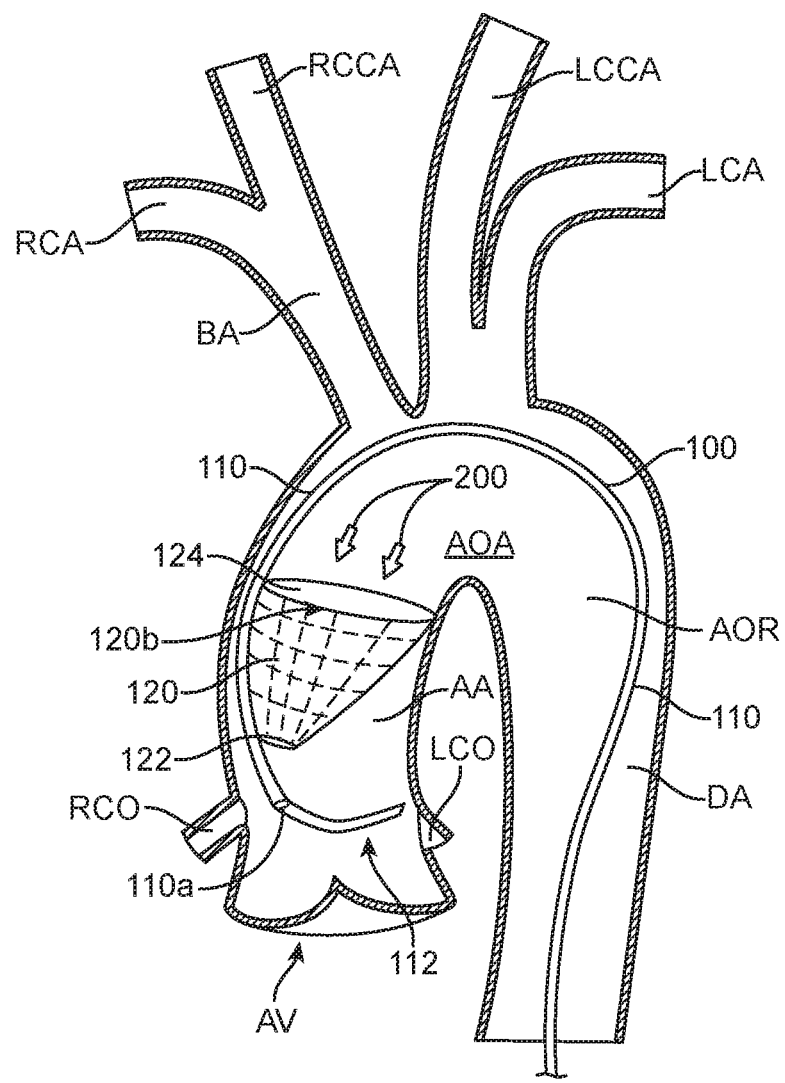
FIG. 2A shows the temporary aortic valve apparatus of FIG. 1A positioned in the ascending aorta of a subject to be in its expanded configuration while the heart is in diastole, according to some embodiments.
Figure 2B:
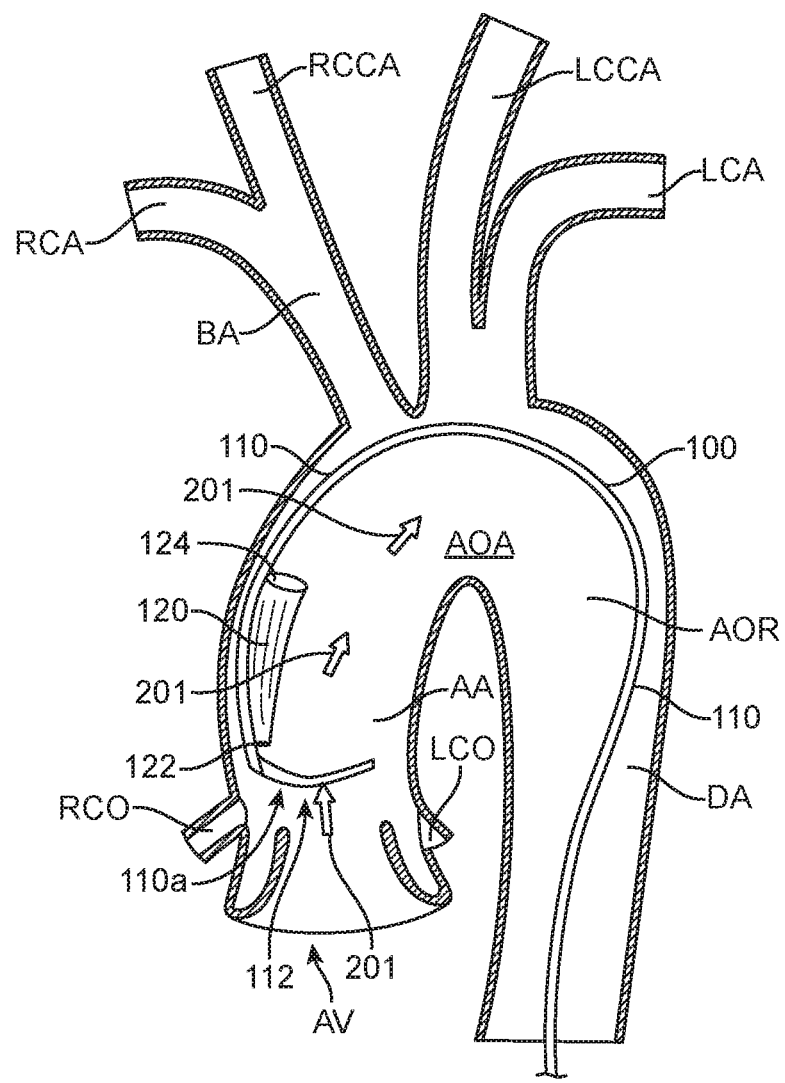
FIG. 2B shows the temporary aortic valve apparatus of FIG. 1A positioned in the ascending aorta of the subject to be in its collapsed configuration while the heart is in systole, according to some embodiments.

FIGS. 2A and 2B show the temporary aortic valve apparatus 100 positioned in the aorta AOR of a subject. In particular, the temporary aortic valve apparatus 100 is positioned in the ascending aorta AA superior to the aortic valve AV. To position the temporary aortic valve apparatus 100 in this location, the temporary aortic valve apparatus may have been introduced percutaneous with a delivery catheter and navigated superiorly in the descending aorta DA and across the arch of the aorta AOA to reach the ascending arota AA. The temporary aortic valve apparatus 100 may be positioned so that the distal opening 122 is superior of the aortic valve AV, the right coronary artery RCA, and the left coronary artery LCA and so that the proximal opening 124 is inferior of the aortic arch AOA and superior of the Sinus of Valsalva. The proximal opening 124 may be positioned to be inferior of the arch of the aorta AOA, the brachiocephalic artery BA (which leads to the right subclavian artery RCA and the right common carotid artery RCCA), the left common carotid artery LCCA, and the left subclavian artery LSA. The large distal loop 112 can be expanded to appose the inner wall of the ascending aorta superior to the Sinus of Valsalva and the coronary ostia to anchor the temporary aortic valve apparatus 100 in place.

In FIG. 2A, the heart is in diastole and the leaflets of the aortic valve AV have closed. In the presence of atrioventricular damage, there would be aortic regurgitation at the aortic valve AV in diastole. The temporary aortic valve apparatus 100 may therefore assume the expanded configuration, with the flexible occluding membrane 120 expanded and the outer circumferential lip of the distal end 120b of the flexible occluding membrane 120 opposing the inner wall of the ascending aorta AA. The flexible occluding membrane 120 may be biased to be in the expanded configuration. Blood flow back toward the aortic valve AV as shown by arrows 200 may pass through the expanded flexible occluding membrane 120 to pass through the openings 124 and 122 to perfuse the right coronary artery RCA and the left coronary artery LCA.

In FIG. 2B, the heart is in systole and the leaflets of the aortic valve AV have opened. Blood flow through the aortic valve AV and aorta AO as indicated by arrows 201 may cause the flexible occluding membrane 120 to collapse and the temporary aortic valve apparatus 100 to therefore assume the collapsed configuration. The large distal loop 112 can continue to anchor and maintain the position the temporary aortic valve apparatus 100 throughout the cardiac cycle in both systole and diastole.

As described above, the temporary aortic valve apparatus 100 will typically be configured to be delivered percutaneous. For example, the temporary aortic valve apparatus 100 may have been delivered transfemorally as shown in FIGS. 2A and 2B. Temporary aortic valve apparatuses of the present disclosure may be configured for other approaches as well. For example, a transaortic approach may be used instead of a transfemoral approach to introduce the temporary aortic valve apparatus 100 to the target location shown in FIGS. 2A and 2B. In other examples, a transapical approach as described below and herein may be used. The temporary aortic valve apparatus 100 will typically be introduced to the target treatment site through the inner lumen of a delivery catheter. The delivery catheter may constrain the flexible occluding membrane 120 to be in its collapsed configuration so that the delivery catheter and the temporary aortic valve apparatus 100 may be navigated through the vasculature in a minimal cross-section configuration or otherwise introduced in a minimal cross-section configuration.

Figure 3A:
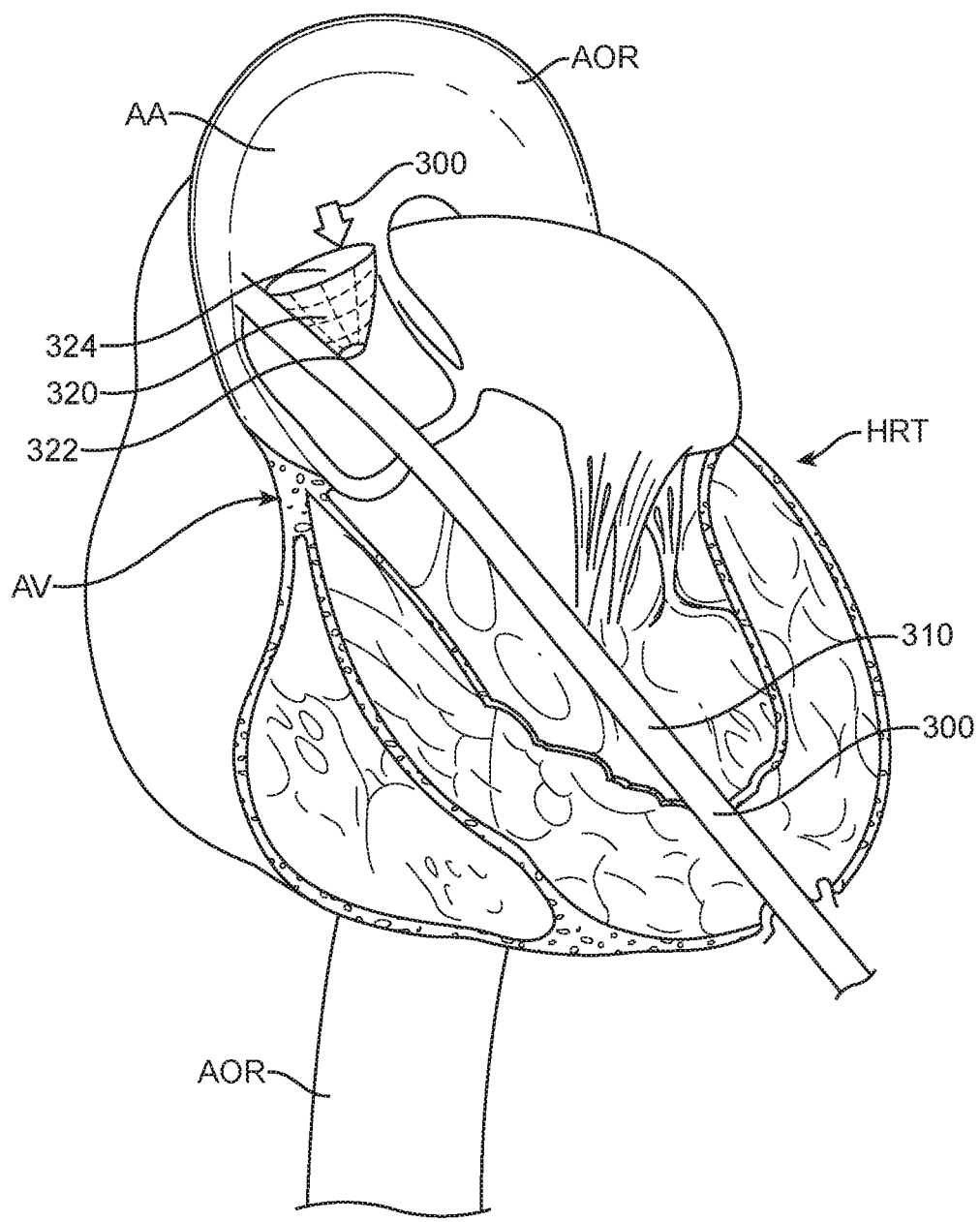
FIG. 3A shows a transapical temporary aortic valve apparatus positioned in the ascending aorta of the subject to be in its expanded configuration while the heart is in diastole, according to some embodiments.

FIG. 3A shows a transapical temporary aortic valve apparatus 300 advanced through the left ventricle of the heart HRT to be positioned in the ascending aorta AA. The transapical temporary aortic valve apparatus 300 may have device components similar to those of the percutaneous temporary aortic valve apparatus 100. The transapical temporary aortic valve apparatus 300 may comprise a catheter shaft 310 coupled to a flexible occluding membrane 320. The flexible occluding membrane 320 may be conical in shape and have a taper in the proximal direction, that is, the distal opening or gap 324 at the distal tip is larger than the proximal opening at the proximal tip of the flexible occluding membrane 320. The distal end of the temporary aortic valve apparatus 300 may have a distal loop, similar to the loop 112 of the temporary aortic valve apparatus 100 described above and herein, to facilitate anchoring within the aorta.

In FIG. 3A, the heart is in diastole and the leaflets of the aortic valve AV have closed. The temporary aortic valve apparatus 300 may therefore assume the expanded configuration, with the outer circumferential lip of the distal end of the flexible occluding membrane 120 opposing the inner wall of the ascending aorta AA. Blood flow back toward the aortic valve AV as shown by arrows 300 may pass through the expanded flexible occluding membrane 320 to pass through the openings 324 and 322 to perfuse the right coronary artery RCA and the left coronary artery LCA.

Figure 3B:
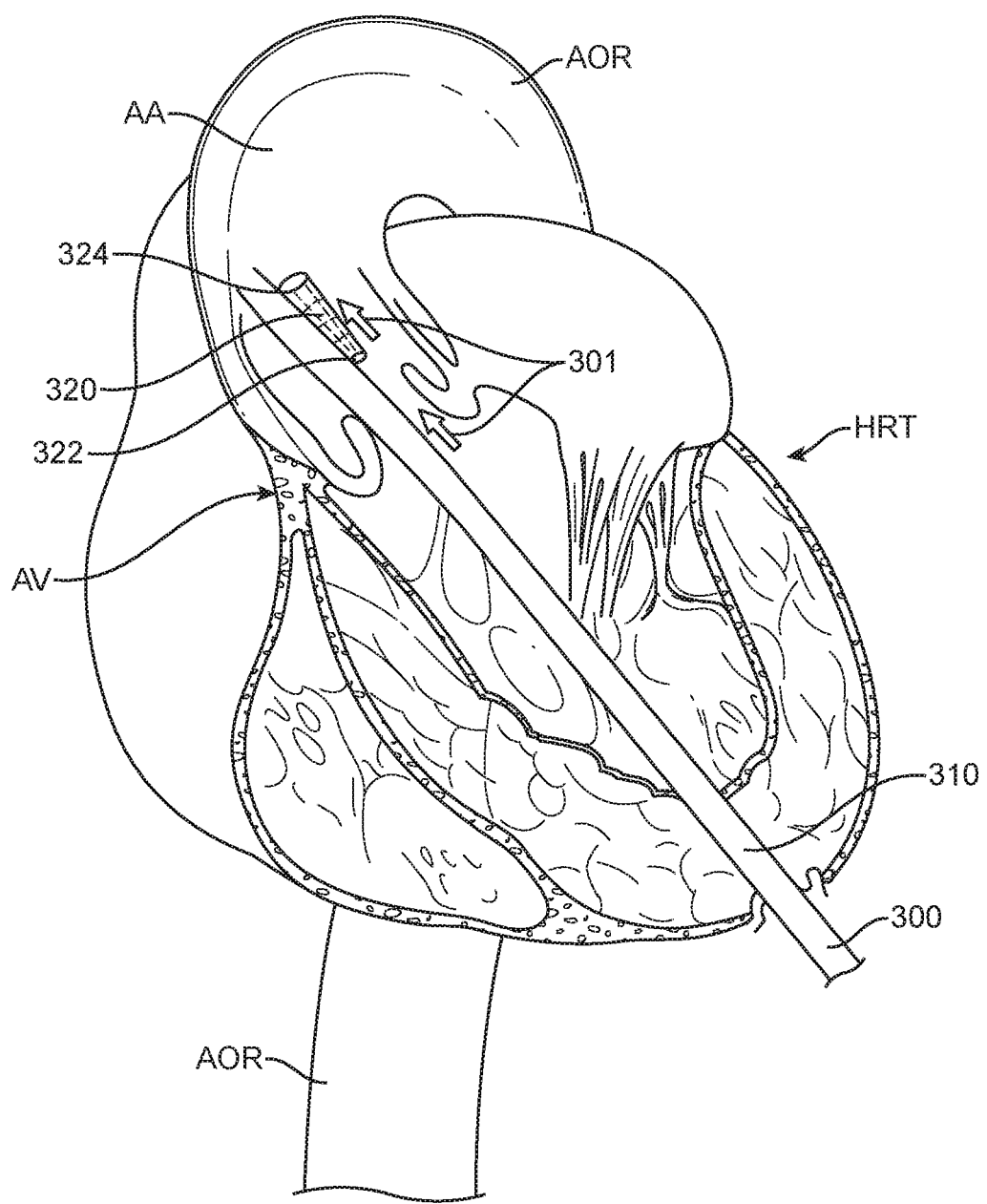
FIG. 3B shows a transapical temporary aortic valve apparatus positioned in the ascending aorta of the subject to be in its collapsed configuration while the heart is in systole, according to some embodiments.

In FIG. 3B, the heart is in systole and the leaflets of the aortic valve AV have opened. Blood flow through the aortic valve AV and aorta AO as indicated by arrows 301 may cause the flexible occluding membrane 320 to collapse and the temporary aortic valve apparatus 300 to therefore assume the collapsed configuration.

Experimental

The inventor has tested a prototype cone-shaped membrane occlusion apparatus substantially the same as the apparatus 100 as described above. Occlusion devices with different gap cross-sectional area to aortic cross-sectional area ratios were tested. Three prototypes with reducing gap:aorta cross-sectional area ratios—35%, 15%, and 0%—were tested in a flow chamber of simulated acute severe aortic regurgitation. Correspondingly, increasing in forward cardiac output volumes, coronary flow:aortic regurgitant volume ratios and reduction in aortic regurgitant volumes were observed ($p<0.001$). Based on such experimentation, an optimal gap:aorta cross-sectional ratio for the cone-shaped membrane occlusion device can be determined. A clinically useful percutaneous device for the management of acute severe aortic regurgitation (e.g., to provide hemodynamic support) may be developed based on this determined optimal ratio.

Figure 4:
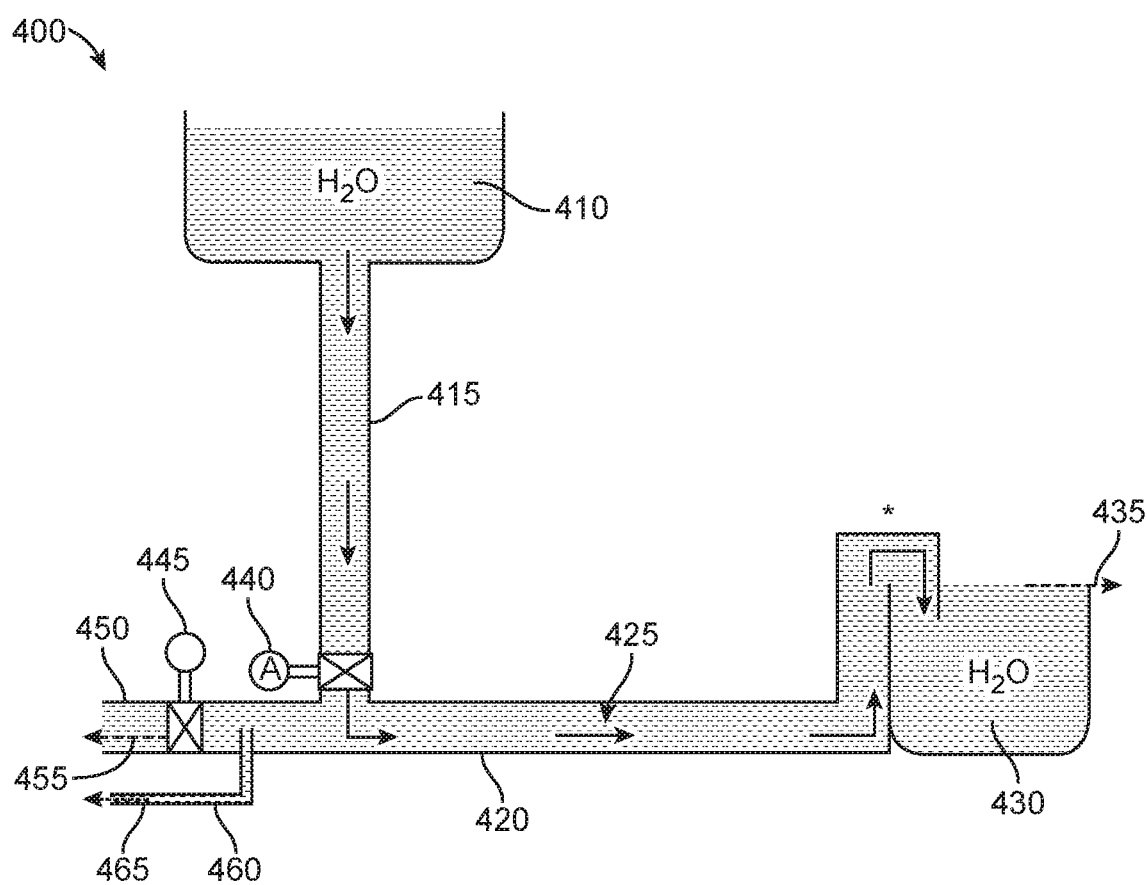
FIG. 4 shows a schematic of a testing apparatus used to test temporary aortic valve apparatuses, according to some embodiments.

FIG. 4 shows a schematic of a testing apparatus 400 used to test the temporary aortic valve apparatuses. The apparatus comprises an input reservoir tank 410 storing fluid which flows through the channel 415 to provide fluid flow to a main channel 420 where the temporary aortic valve testing site 425 is located. The fluid may also flow through the main channel 420 to an output reservoir tank 430 and a cardiac output volume measurement apparatus 435. On the opposite side, the fluid may also flow through the main channel 420 through channel 450 which leads to an aortic regurgitant volume measurement apparatus 455. The fluid may also flow through the main channel 420 through a channel 460 leading to a coronary flow volume measurement apparatus 465. The channels 415, 420, and 450 may comprise clear polyvinyl chloride (PVC) tubing with a 2.54 cm internal diameter and the channel 460 may also comprise a clear polyvinyl chloride (PVC) tubing but with a 0.635 cm internal diameter. The PVC tubings used may be obtained from Kuriyama of America, Inc. of Schaumburg, Ill.

The testing apparatus 400 may further comprise valves (e.g., electrically actuated ball valves 24VAC available from Dynaquip Controls Corp. of St. Clair, Mich.) 440 and 445. The valve 440 may separate the channel 415 and the main channel 420. The valve 445 may separate the main channel 420 with the channel 450. When the valve 445 is open, fluid may be allowed to flow through the channel 450 to reach the aortic regurgitant volume measurement apparatus 455. When the valve 445 is open, more fluid is allowed to flow through the channel 460 to reach the coronary flow volume measurement apparatus 460.

The valves 440, 445 may be open and closed to provide pulsatile fluid flow through the main channel 420, simulating the pulsatile blood flow in the aorta. Pulsatile flow conditions of the ascending aorta with or without induced aortic regurgitation (AR) may be simulated. The automatic and adjustable timing cycles of the two valves 440, 445 may be created via an electrical circuit with a repeat cycle time delay relay (e.g., available from Dayton Electric Co. of Niles, Ill.) and two control transformers 120/24 VAC (e.g., available from Veris Industries of Portland, Oreg.). The two valves 440, 445 may be coordinated such that normal flow conditions with an intact aortic valve and acute wide-open aortic regurgitation can be simulated at the testing site 425.

The tested temporary aortic valve (TAV) apparatus 100 comprised a cone-shaped latex membrane 120 having a thickness of 0.33 mm. The membrane 120 was affixed to a standard 5-Fr. standard catheter 110. The dimensions of the latex cone were as follows: the diameter of the cone-opening (circular lip) at the proximal end 120b was slightly larger than the diameter of the inner tubing wall (2.54 cm) at the test site 425 representing the ascending aorta. The slightly larger size was chosen to ensure sufficient apposition of the conical membrane 120 to the aorta during diastole when the conical membrane 120 is open. The depth of the conical membrane, from proximal lip to distal tip, was arbitrarily set at 5 cm. The gap or opening 122 was created by cutting the tip of the conical membrane 120 such that the cross-sectional area of the gap-opening 122 with respect to the aorta can be specified.

While certain dimensions, parameters, and component materials of the tested temporary aortic valve (TAV) apparatus 100 are disclosed above, it is to be understood that such dimensions, parameters, and component materials are provided as examples only. It will be understood that in practice, the temporary aortic valve apparatus 100 may encompass a variety of dimensions, parameters, and component materials without departing from the scope of the present disclosure.

Figure 5A:
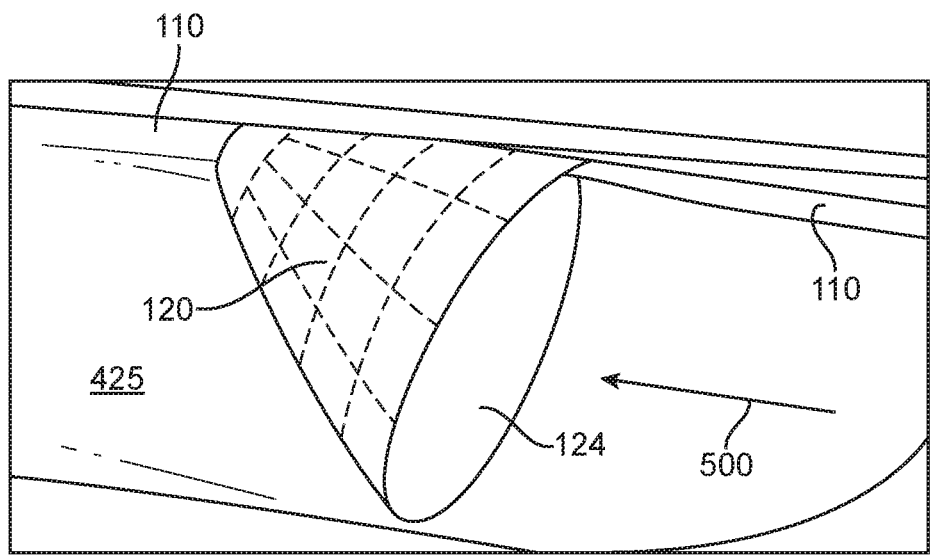
FIG. 5A shows the temporary aortic valve apparatus of FIG. 1A in its expanded configuration in the testing apparatus of FIG. 4 when simulating diastole.

FIG. 5A shows the temporary aortic valve apparatus 100 in its expanded configuration in the testing site 425 of the testing apparatus 400 when simulating diastole. Retrograde fluid flow in the direction indicated by arrow 500 can enter the proximal opening 124 to expand the flexible occluding membrane 120. Alternatively or in combination, the conical membrane 120 may also assume its original expanded configuration in the absence of forward fluid flow. The conical membrane 120 in the expanded configuration may provide retrograde resistance to aortic regurgitation while the pre-fabricated gap 122 may control residual aortic regurgitation and allow for coronary filling.

Figure 5B:
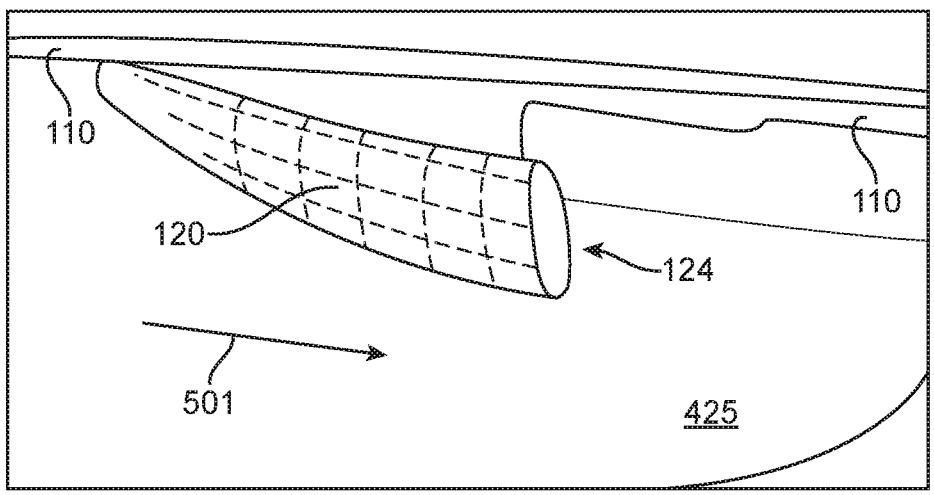
FIG. 5B shows the temporary aortic valve apparatus of FIG. 1A in its collapsed configuration in the testing apparatus of FIG. 4 when simulating systole.

FIG. 5B shows the temporary aortic valve apparatus 100 in its collapsed configuration in the testing site 425 of the testing apparatus 400 when simulating systole. Forward fluid flow in the direction indicated by arrow 501 collapses the flexible occluding membrane 120.

Flow volumes were collected at respective sites representing the forward cardiac output, aortic regurgitant flow, and coronary flow over a 1-minute run comprising 12 cycles. Volumes were measured under the conditions of baseline normal (with intact aortic valve; ball-valve (B) closed throughout cycles), simulated acute severe aortic regurgitation (AR) (alternating opening and closing of ball-valves (A) and (B) per cycle) and acute severe AR with TAV protection. The TAV prototypes tested had 35%, 15%, and 0% gap:aorta cross-sectional area ratios at the cone-tip, respectively. Data for each condition was averaged over 3 runs. All volume measurements were collected in liters (l). Statistical analyses of the volume differences during the various conditions were performed using ANOVA.

Results. The three prototypes with reducing gap:aorta cross-sectional area ratios (35%, 15%, 0%) were tested in the flow chamber of simulated acute severe aortic regurgitation (e.g., the testing apparatus 400). Correspondingly, increasing in forward cardiac output volumes, coronary flow:aortic regurgitant volume ratios and reduction in aortic regurgitant volumes were observed (p<0.001). The large distal catheter loop of the prototype devices were successful in immobilizing the conical membrane from any undue axial movements along the length of the tubing or mock "aorta."

FIG. 6 shows a table of the experimental results. Compared to the normal baseline normal condition, simulated acute severe AR showed a drop in the forward cardiac output volume (from 21.12±0.49 to 14.43±0.18), decrease in the coronary flow volume (from 1.97±0.06 to 1.78±0.01) and a sharp presence of aortic regurgitant volume (From 0 to 8.07±0.08).

With membrane TAV protection during simulated acute severe AR, there was a significant increase in the forward cardiac output volumes as the TAV gap size decreased from 35% to 0% (p<0.001). Along with the smaller TAV gap sizes, the aortic regurgitant volume significantly decreased while the coronary flow:aortic regurgitant ratio significantly increased (both with p<0.001). The absolute coronary flow volume did not drop with TAV deployment of any gap size.

It will be understood that the results were conducted with the prototype TAV apparatus 100 and that variations to the experimental results may occur with different testing parameters and/or modifications to the TAV apparatus 100. The experimental results are provided as examples.

Discussion. Prior 3-balloon TAV devices were also studied. These 3-balloon TAV devices may be challenged due to the fixed nature of the gap provided. (Ho P C, Minim Invasiv Ther Allied Technol 2008; Ho P C, J Med Eng Technol 2011; Ho P C, J Heart Valve Dis 2013.) During systole, the fixed TAV gaps from the inflated balloons may represent forward aortic flow resistance and may affectively create an artificial stenosis. Although calculated at moderate range, the effective TAV aortic stenosis could limit its application in patients with a compromised left ventricle. Subsequent addition of balloon counter-pulsation to the balloon-based TAV device, however, could potentially lessen forward aortic flow resistance. (Ho P C, Minim Invasive Ther Allied Technol 2011.)

The TAV devices of the present disclosure may include conical membranes that may be collapsible during systole and fully expandable in diastole based on the passive forces of the aortic flow, with a gap-to-aorta cross-sectional area ratio that can be tailored to optimize aortic regurgitation protection and coronary flow. The conical membrane of the tested TAV device may have a shape may cause the lip of the conical membrane to be in apposition with the aortic (tubing) wall, such that the diastolic regurgitant flow (for coronary filling) could be controlled at the pre-specified gap at the cone-tip. The elegance of the conical membrane temporary aortic valve was demonstrated by the collapsibility of the conical membrane due to the passive forces of the aortic flow. As the lip of the conical membrane becomes in apposition with the tubing or mock "aortic" wall during diastole, diastolic regurgitant flow (e.g., for coronary filling) could be controlled at the pre-specified opening or cap at the membrane tip. Without the concern for systolic flow obstruction in the test system versus in vivo, a lower limit of the gap:aorta cross-sectional area could be determined. Because the mathematical model for the 3-balloon TAV model calculated the gap to be at 35% of the aortic cross-sectional area, the selection for the membrane TAV gap sizes in this study began at 35%, followed by 15%, and 0%. While these specific gap size percentages were tested, other TAV gap sizes such as 50%, 40%, 30%, 20%, or 10% are also contemplated.

The 0% TAV gap was chosen as a control for the study construct including the flow apparatus and the membrane TAV prototype. Ideally, no AR would be expected at 0% TAV gap. In the experiment using the TAV with 0% gap, however, the aortic regurgitant volume was quite high even though it was much less than using TAV with larger gaps (table 1, FIG. 6). The excessive AR findings may be explained by the TAV prototype assembly 100 and the experimental setup 400. The imperfect seal of the TAV prototype 100 may be caused by inadequate apposition of the cone-lip to the tubing wall and/or device-related malapposition against the tubing wall. In this regard, the TAV devices of the present disclosure may be manufactured to provide improvements over the tested, pre-clinical TAV prototype device based on factors such as membrane material selection, catheter stiffness and french-size selection, and mounting technique of the membrane to the catheter 110.

With decreasing TAV gap sizes, the gradual improvements in the forward cardiac output volumes and reduction in the aortic regurgitant volumes are encouraging results. The lack of coronary flow volume response can be viewed as a positive finding in conjunction with the improvements in the coronary:regurgitant volume ratios. Unintentional allowance of significant AR by the membrane TAV prototype may explain this lack of coronary flow improvement, which may improve with further manufacturing as mentioned. In a published study of a temporary valve with no built-in gaps, however, device deployment caused further decline in coronary flow rates already compromised by induced acute aortic regurgitation (Salizzoni S, J Thorac Cardiovasc Surg 2009). Our membrane TAV prototype 100 did not reduce the coronary flow during deployment while sustaining a significant reduction in aortic regurgitation.

Refinement of the gapped device may be contingent upon redefining the low-limit for the size of the gap 122 in the membrane TAV device 100, such that it can provide the maximal AR protection without restricting coronary flow. With this approach of device optimization, the coronary flow could rise at improved TAV AR protection. The high speed of the aortic regurgitant jet has been attributed to coronary flow reduction at severe range acute AR. Reversal of diastolic coronary flow due to Venturi effect from the high speed regurgitant jet has been suggested (Ardehali A, J Am Coll Cardiol 1995). Our in vitro flow apparatus 400 also may not be able to reproduce the physiologic "suction" wave of coronary microvasculature in diastolic filling (Davies J E, Circulation 2006). By reducing the speed of the aortic regurgitant flow with the membrane TAV, diastolic coronary filling could be optimized by lessening likelihood for coronary flow reversal in significant AR. The regurgitant blood volume may be more likely to enter the coronary bed with its lower outflow pressure in the right atrium and its "suction" effect of diastolic filling versus the left ventricle.

The study performed may also be limited by the typical inability of in vitro flow models such as the flow model 400 to completely simulate physiologic conditions. Also, the TAV prototype 100 used was an approximation of the pre-clinical vision with contemplated improvements in material selection and manufacturing processes as discussed. As such, the study provides qualitative proof of concept evaluation of a promising membrane transcatheter TAV device 100. The findings suggest a lower limit for the gap:aorta dimensional ratio could be determined to optimize aortic regurgitation protection while allowing for optimal diastolic coronary filling.

While preferred embodiments of the present disclosure have been shown and described herein, it will be obvious to those skilled in the art that such embodiments are provided by way of example only. Numerous variations, changes, and substitutions will now occur to those skilled in the art without departing from the present disclosure. It should be understood that various alternatives to the embodiments of the present disclosure described herein may be employed in practicing the present disclosure. It is intended that the following claims define the scope of the invention and that methods and structures within the scope of these claims and their equivalents be covered thereby.

What is claimed is:

1. A temporary cardiovascular valve apparatus comprising:
   a catheter shaft adapted for placement within an artery of a patient; and
   a flexible membrane having a lateral side coupled to the catheter shaft, a proximal end, a distal end, and an opening at the distal end,
   wherein the flexible membrane is adapted to, when placed within the artery with the distal end of the flexible membrane oriented toward blood flow within the artery, alternate between an expanded occluding configuration and a collapsed configuration in response to the blood flow and in synchrony with ventricular diastole and systole,
   wherein the flexile membrane inhibits the blood flow within the artery when in the expanded occluding configuration and lessens inhibition of the blood flow when in the collapsed configuration, and
   wherein the opening allows blood perfusion therethrough when the membrane is in the expanded occluding configuration within the artery.

2. The temporary cardiovascular valve apparatus of claim 1, wherein the opening is positioned at substantially a center of the membrane.

3. The temporary cardiovascular valve apparatus of claim 2, wherein the center of the membrane is disposed at the distal end of the membrane.

4. The temporary cardiovascular valve apparatus of claim 1, wherein the opening is positioned at a location offset from a center of the membrane.

5. The temporary cardiovascular valve apparatus of claim 1, wherein the membrane has a plurality of openings to allow blood perfusion therethrough when in the expanded occluding configuration.

6. The temporary cardiovascular valve apparatus of claim 1, wherein the opening has a cross-sectional size of 50% or less, 45% or less, 40% or less, 35% or less, 30% or less, 25% or less, 20% or less, 15% or less, 10% or less, or 5% or less of the artery.

7. The temporary cardiovascular valve apparatus of claim 1, wherein the catheter shaft comprises a distal anchoring loop having an expanded curved configuration for anchoring the catheter shaft and the membrane in the aorta and a collapsed, straightened configuration for advancement into or retraction from the artery.

8. The temporary cardiovascular valve apparatus of claim 1, wherein the membrane has a conical shape.

9. The temporary cardiovascular valve apparatus of claim 8, wherein the conically-shaped membrane comprises an annular proximal lip adapted to appose an inner wall of the artery when the membrane is in the expanded occluding configuration.

10. The temporary cardiovascular valve apparatus of claim 1, wherein the membrane is adapted to be positioned within an ascending aorta of the patient to provide occlusion therein.

11. The temporary cardiovascular valve apparatus of claim 10, wherein the membrane is adapted to be positioned within the ascending aorta just above the Sinus of Valsalva and coronary ostia.

12. The temporary cardiovascular valve apparatus of claim 10, wherein the membrane is adapted to be positioned within the ascending aorta between the coronary ostia and the brachiocephalic artery.

\* \* \* \* \*